(12) United States Patent
Weinstein

(10) Patent No.: US 7,189,746 B2
(45) Date of Patent: Mar. 13, 2007

(54) METHODS FOR PROMOTING WOUND HEALING

(75) Inventor: David E. Weinstein, Dobbs Ferry, NY (US)

(73) Assignee: GliaMed, Inc., New York, NY (US)

( * ) Notice: Subject to any disclaimer, the term of this patent is extended or adjusted under 35 U.S.C. 154(b) by 500 days.

(21) Appl. No.: 10/290,657

(22) Filed: Nov. 8, 2002

(65) Prior Publication Data

US 2004/0092440 A1  May 13, 2004

(51) Int. Cl.
*A61K 31/4245* (2006.01)

(52) U.S. Cl. ..................................... 514/364

(58) Field of Classification Search ............... None
See application file for complete search history.

(56) References Cited

OTHER PUBLICATIONS

Adlkofer and Lai, "Role of neuregulins in glial cell development.", Glia, 29:104-11, 2000.
Asahina et al., "Modulation of Lanferhans cell function by epidermal nerves," J. Allergy Clin. Immunol., 96: 1178-82, 1995.
Beers and Berkow, eds., "The Merck Manual of Diagnosis and Therapy." 17th ed. (Whitehouse Station, NJ: Merck Research Laboratories, 1999), chap. 183.
Castagnino et al., "Neu differentiation factor / heregulin induction be hepatocyte and keratinocyte growth factors," Oncogene, 19: 640-48, 2000.
Cohen, "Stress and wound healing," Acta Anat. (Basel), 103: 134-41, 1979.
Danilenko et al., Neu differentiation factor upregulates epidermal migration and integrin expression in excisional wounds, J. Clin. Invest., 95: 842-51, 1995.
Easter et al., Initial tract formation in the mouse brain, J. of Neurosci., 13: 285-99, 1993.
Galat and Metcalfe, "Peptidylproline cis/trans isomerases," Prog. Biophys. Mol. Biol., 63: 67-118, 1995.
Gold B.G., "FK 506 and the role of immunophilins in nerve regeneration," Mol. Neurobiol., 15: 285-306, 1997.
Gondré et al., "Accelerated nerve regeneration mediated by Schwann cells expressing a mutant form of the POU protein SCIP," J. Cell Biol., 141: 493-501, 1998.
Hamilton and Steiner, "Immunophilins: beyond immunosuppression," J. Med. Chem., 41: 5119-43, 1998.
Hom et al., "Growth factor therapy to improve soft tissue healing," Facial Plast Surg., 18: 41-52, 2002.
Hsieh and Lin, "Modulation of keratinocyte proliferation by skin innervation," J. Invest. Dermatol., 113: 579-86, 1999.
Huang et al., "Influence of cutaneous nerves on keratinocyte proliferation and epidermal thickness in mice," Neuroscience, 94: 965-73, 1999.
Hsieh et al., "Epidermal denervation and its effects on keratinocytes and Langerhans cells," J. Neurocytol., 25: 513-24, 1996.
Jost et al., "Acceleration of peripheral nerve regeneration following FK 506 administration," Restor. Neurol. Neurosci., 17: 39-44, 2000.
Kay, J.E., "Structure-function relationships in the FK506-binding protein (FKBP) family of peptidylprolyl cis-trans isomerases," Biochem. J., 314: 361-85, 1996.
Li, et al., "Sensory and motor denervation influence epidermal thickness in rat foot glabrous skin," Exp. Neurol., 147: 452-62, 1997.
Light and Perl, "Peripheral Sensory System", In Peripheral Neuropathy, Dyck, P.J. and Thomas, P.K., eds., (Philadelphia: W.B. Saunders Company, 1993).
Marks, A.R., "Cellular functions of immunophilins," Physiol. Rev., 76: 631-49, 1996.
Mihara, M., "Regenerated cutaneous nerves in human epidermal and subepidermal regions. An electron microscopy study," Arch. Dermatol. Res., 276: 115-22, 1984.
Monteiro-Riviere et al., "Interspecies and interregional analysis of the comparative histologic thickness and laser Doppler blood flow measurements at five cutaneous sites in nine species," J. Invest. Dermatol., 95: 582-86, 1990.
Monteiro-Riviere et al., "Laser Doppler measurements of cutaneous blood flow in ageing mice and rats," Toxicol. Lett., 57: 329-38, 1991.
Niemann et al., "Hepatocyte growth factor and neuregulin in mammary gland cell morphogenesis," Adv. Exp. Med. Biol., 480: 9-18, 2000.
Stanulis-Praeger and Gilchrest, "Growth factor responsiveness declines during adulthood for human skin-derived cells," Mech. Ageing Dev., 35: 185-98, 1986.
Steinman and Inaba, The Binding of antigen presenting cells to T lymphocytes, Adv. Exp. Med. Biol., 237: 31-41, 1988.
Steiner et al., "Neurotrophic immunophilin ligands stimulate structural and functional recovery in neuridegenerative animal models," Proc. Natl. Acad. Sci. USA, 94: 2019-24, 1997.
Strauch et al., "Antologous Schwann cells drive regeneration through a 6-cm autogenous venous nerve conduit," J. Reconstr. Microsurg., 17: 589-95, 2001.
Taylor et al., "Involvement of follicular stem cells in forming not only the follicle but also the epidermis," Cell, 102: 451-61, 2000.
Weinstein, D.E., "The role of Schwann cells in neural regeneration," The Neuroscientist, 5: 208-16, 1999.
Weinstein et al., "Molecular mechanism of nerve infection in leprosy," Trends Microbiol., 7: 185-86, 1999.
Werner and Smola, "Paracrine regulation of keratinocyte proliferation and differentiation," Trends Cell Biol., 11: 143-46, 2001.
Wu et al., "The POU gene brn-5 is induced by neuregulin and is restricted to myelinating Schwann cells," Mol. Cell Neurosci., 17: 683-95, 2001.
Xian and Zhou, "Roles of transforming growth factor-alpha and related molecules in the nervous system," Mol. Neurobiol., 20: 157-83, 1999.

*Primary Examiner*—Phyllis G. Spivack
(74) *Attorney, Agent, or Firm*—Sande Rabin

(57) ABSTRACT

The present invention provides methods for promoting healing of a wound in a and for promoting regeneration of epithelial tissue in a subject comprising administering an effective amount of 2,2'-(1,3,4-oxadiazole-2,5-diyl)bis[1-(3,3-dimethyl-1,2-dioxopentyl)-pyrrolidine (GM-284).

27 Claims, 11 Drawing Sheets

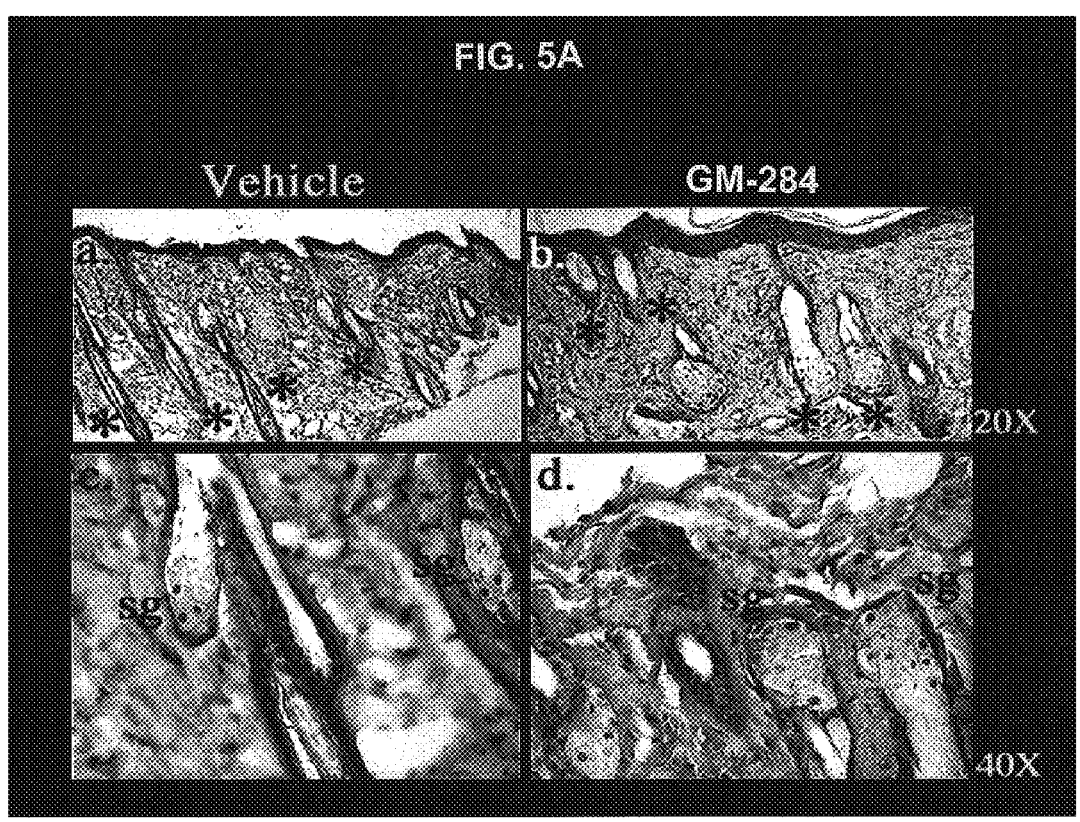

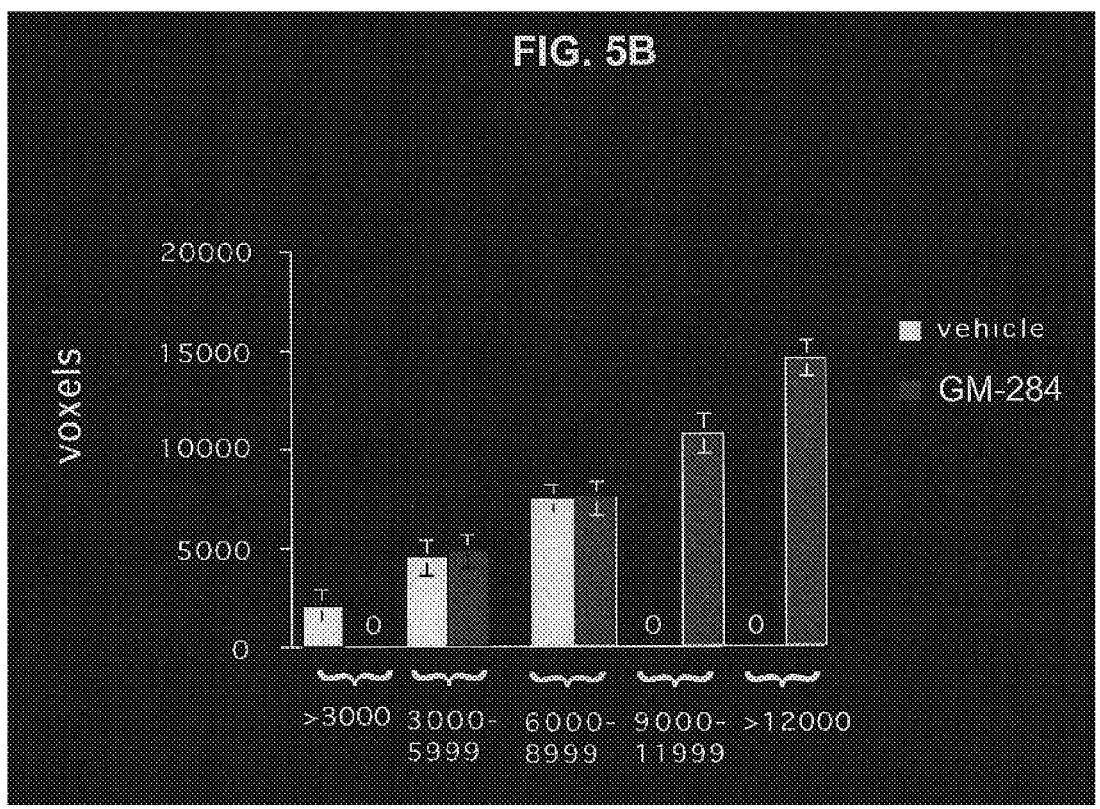

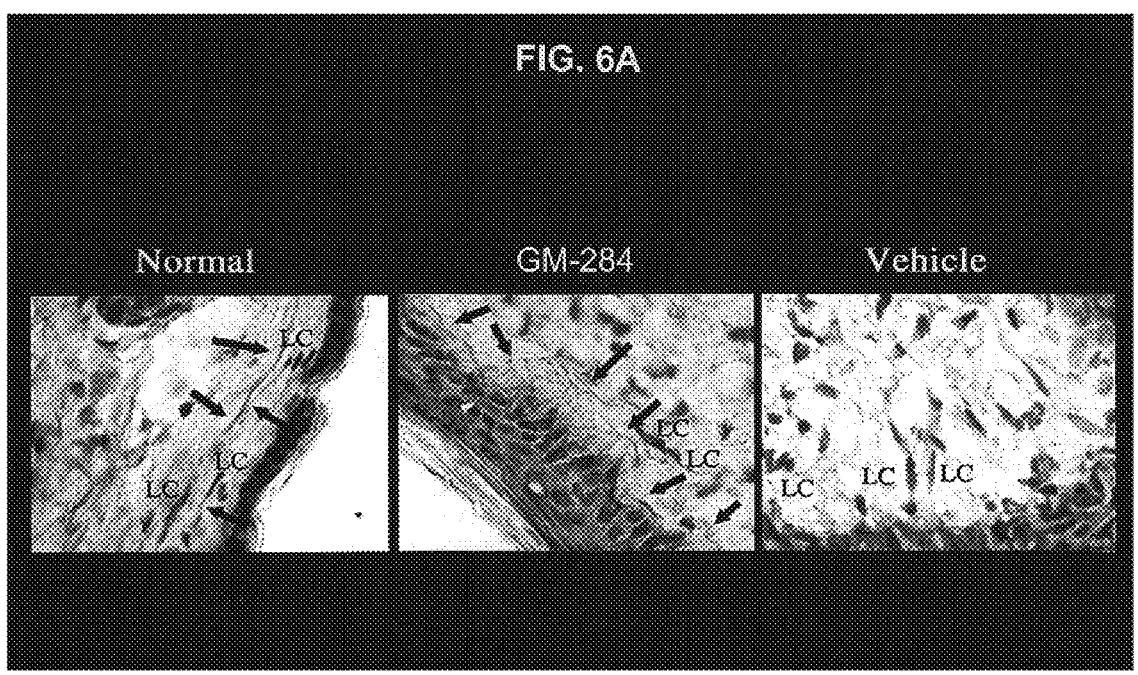

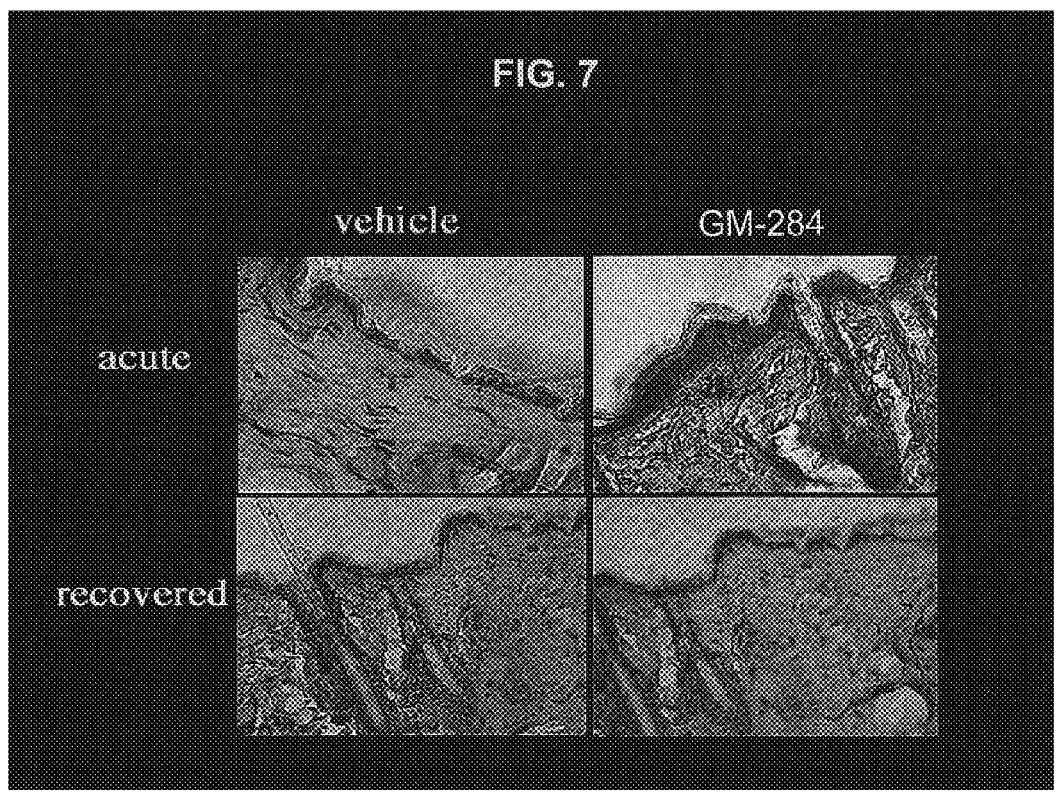

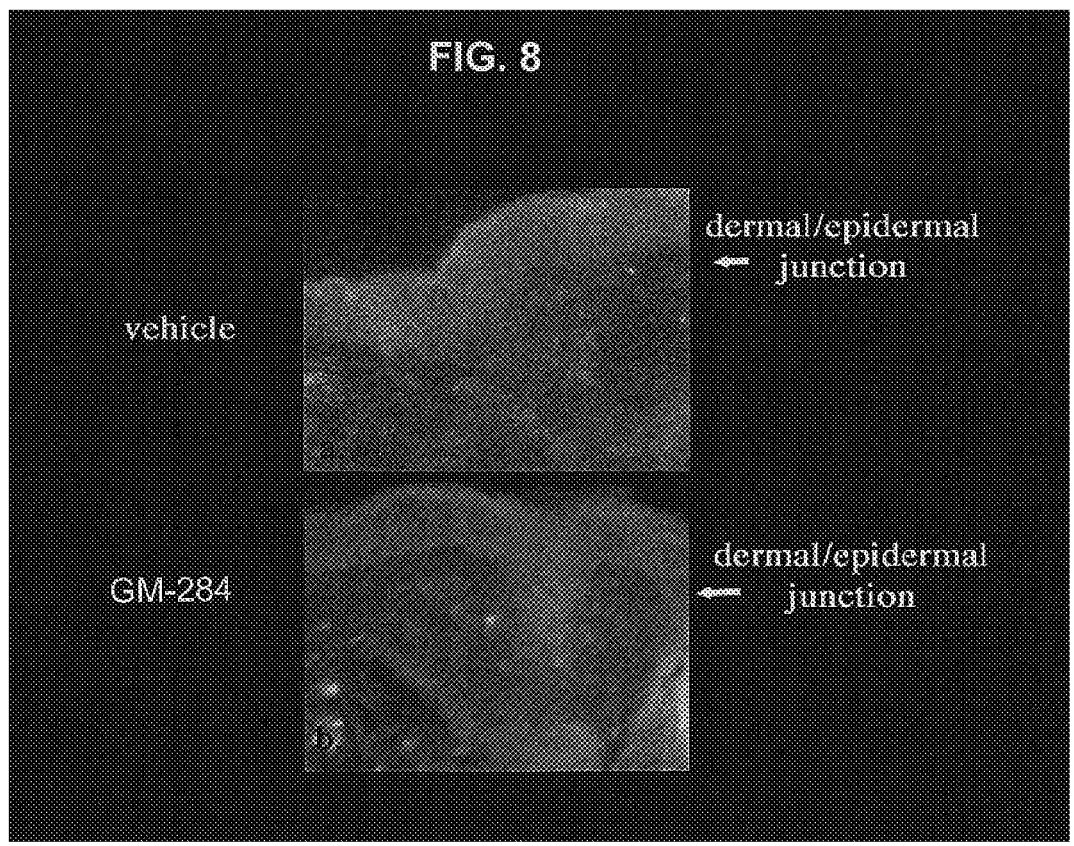

METHODS FOR PROMOTING WOUND HEALING

INCORPORATION BY REFERENCE

This application hereby incorporates by reference, in its entirety, U.S. patent application entitled, "METHODS FOR INDUCING REGENERATION, REMYELINATION, AND HYPERMYELINATION OF NERVOUS TISSUE", application Ser. No. 10/290,654, filed concurrently on Nov. 8, 2002.

BACKGROUND OF THE INVENTION

Healing of wounds in skin and other epithelia involves a complex set of interactions between numerous components, including epithelial cells, peripheral nerves, and immune cells, as well as soluble and matrix molecules contributed by the various cell types (reviewed in Hom et al., Growth factor therapy to improve soft tissue healing. *Facial Plast. Surg.*, 18:41–52, 2002). Dysfunctions associated with one or more of these components can lead to anatomical changes of intact skin and/or alterations in the ability of wounded epithelium to regain its normal histology and function. For example, sensory denervation of skin results in alterations in skin anatomy, including thinning of the epidermis, decreases in epidermal proliferation, and changes in the gene expression of Langerhans cells (Huang et al., Influence of cutaneous nerves on keratinocyte proliferation and epidermal thickness in mice. *Neuroscience*, 94:965–73, 1999; Hsieh et al., Epidermal denervation and its effects on keratinocytes and Langerhans cells. *J. Neurocytol.*, 25:513–24, 1996; Li et al., Sensory and motor denervation influence epidermal thickness in rat foot glabrous skin. *Exp. Neurol.*, 147: 452–62, 1997; Laplante et al., Mechanisms of wound reepithelialization: hints from a tissue-engineered reconstructed skin to long-standing questions. *FASEB J.*, 15:2377–89, 2001). Therefore, sensory denervation of skin can produce an underlying environment that is predisposed to the establishment of wounds that are refractory to healing.

There are several clinical examples, including diabetic and pressure ulcers, in which a similar sequence of events appears to play a significant role. The importance of dermal innervation was actually understood in ancient times, and described in detail in the Bible: leprosy, a disease of the peripheral nerves that leads to erosive, chronic skin lesions (Weinstein et al., Molecular mechanism of nerve infection in leprosy. *Trends Microbiol.*, 7:185–86, 1999), is the first lesion for which this pattern was described.

Normal keratinocytes have a relatively high, age-dependent proliferative index. However, epidermal thickness is maintained at a relatively constant level throughout most of life, suggesting that an equilibrium exists among keratinocyte cell birth, squamae formation, and sloughing of the stratum corneum (Stanulis-Praeger and Gilchrest, Growth factor responsiveness declines during adulthood for human skin-derived cells. *Mech. Ageing Dev.*,35:185–98, 1986; Laplante et al., Mechanisms of wound reepithelialization: hints from a tissue-engineered reconstructed skin to long-standing questions. *FASEB J.*, 15:2377–89, 2001). This equilibrium is highly influenced by innervation of the skin. Hsieh and colleagues have shown that, within seventy-two hours of denervation, there is a marked and significant thinning of the epidermis (Hsieh and Lin, Modulation of keratinocyte proliferation by skin innervation. *J. Invest. Dermatol.*, 113:579–86, 1999), raising the possibility that denervation negatively affects the keratinocyte mitotic index. In the same study, Hsieh and colleagues examined BrdU incorporation in denervated rat skin. They noted that it was reduced to almost half of the incorporation on the contralateral side of the same animal, and that epidermal thickness was reduced by 70% within four days (Hsieh and Lin, Modulation of keratinocyte proliferation by skin innervation. *J. Invest. Dermatol.*, 113:579–86, 1999). These data are consistent with a model in which denervation of the skin leads to a reduction in keratinocyte growth, resulting in epidermal thinning.

Importantly, the alterations in keratinocyte and Langerhans cell anatomy and functionality are reversible. By three months following mechanical nerve transection, axons have regenerated into denervated areas, and epidermal thickness has returned to baseline, as has the keratinocyte proliferative rate (Huang et al., Influence of cutaneous nerves on keratinocyte proliferation and epidermal thickness in mice. *Neuroscience*, 94:965–73, 1999).

One possible explanation for the above findings is that, in the absence of sensory innervation, there is a decrease in blood flow to the target field. Such an alteration may result in either the accumulation of inhibitory molecules—which would then negatively affect keratinocyte growth—or a reduction in the delivery of one or more growth factors to the dermal/epidermal boundaries—which might also reduce keratinocyte proliferation. This hypothesis is consistent with the known pathophysiology of diabetes, in which there is microvascular damage, peripheral neuropathy, and thinning of the skin, with a propensity toward the development of ulcers. However, while it is an attractive hypothesis, it lacks support in the literature.

For example, Monteiro-Riviere and colleagues have demonstrated in a number of species that there is no correlation between blood flow and epidermal thickness (Monteiro-Riviere et al., Interspecies and interregional analysis of the comparative histologic thickness and laser Doppler blood flow measurements at five cutaneous sites in nine species. *J. Invest. Dermatol.*, 95:582–86, 1990; Monteiro-Riviere et al., Laser Doppler measurements of cutaneous blood flow in ageing mice and rats. *Toxicol. Lett.*, 57:329–38, 1991). Thus, the epidermal thinning that occurs after denervation appears to result from a direct inter-relationship between sensory fibers and keratinocytes. The foregoing observations also raise questions as to the perceived etiology of stasis ulcers. While the dogma holds that decubital ulcers are the result of poor blood flow and blood pooling in the skin, this has never been demonstrated or tested rigorously. Given the above-described data, it is possible that these ulcers develop as a result of pressure-induced peripheral nerve damage and subsequent thinning of the skin.

The findings discussed above do not address whether it is the axons per se, their associated Schwann cells, or both, that influence keratinocyte biology. However, consistent with other examples of nerve regeneration (Gondré et al., Accelerated nerve regeneration mediated by Schwann cells expressing a mutant form of the POU protein SCIP. *J. Cell Biol.*, 141:493–501, 1998; Weinstein, D. E., The role of Schwann cells in neural regeneration. *The Neuroscientist*, 5:208–16, 1999; Weinstein et al., Molecular mechanism of nerve infection in leprosy. *Trends Microbiol.*, 7:185–86, 1999; Strauch et al., The generation of an artificial nerve, and its use as a conduit for regeneration. *J. Reconstr. Microsurg.*, 17:589–98, 2001), regenerating sensory fibers in the skin grow only in association with Schwann cells (Mihara, M., Regenerated cutaneous nerves in human epidermal and subepidermal regions. An electron microscopy study. *Arch. Dermatol. Res.*, 276:115–22, 1984), suggesting that the Schwann cells play an integral role in wound healing. This possibility is further supported by the observation that glial growth factor (GGF) (also known as NDF and ARIA), which is secreted by Schwann cells following injury (Carroll et al., Expression of neuregulins and their putative receptors, ErbB2 and ErbB3, is induced during Wallerian degeneration. *J. of Neurosci.*, 17:1642–59, 1997), stimulates keratinocyte proliferation and increases epidermal thickness (Danilenko et al., Neu differentiation factor upregulates epidermal migration and integrin expression in excisional wounds. *J. Clin. Invest.*, 95:842–51, 1995).

Refractory skin lesions present a huge therapeutic challenge in patients with a range of underlying pathologies, including diabetic ulcers, venous stasis ulcers, pressure ulcers, burns, and trauma. The possibility of increasing the rate of surgical wound closure represents another, related, challenge, for such an increase would provide the benefit of limiting post-operative wound infection. Finally, great benefit would be derived from a means of enhancing reinnervation of healing skin, as this would likely limit paresthesias resulting from failed nerve regeneration. To meet some of these challenges, investigators have developed therapies that merely stimulate simple re-epithelialization. This approach, while offering some benefit, is limited, as epidermis will break down in the absence of repair of the underlying tissue. Accordingly, given the huge clinical implications associated with wound healing, there exists a need to develop a new, satisfactory therapy that will achieve more than mere stimulation of simple re-epithelialization.

SUMMARY OF THE INVENTION

The present invention is based on the discovery that FK506-related compounds, particularly nonimmunosuppressive derivatives of FK506 such as GM-284, 2,2'-(1,3,4-oxadiazole-2,5-diyl)bis[1-(3,3-dimethyl-1,2-dioxopentyl)-pyrrolidine (GM-284) stimulate growth of keratinocytes independently, and also stimulate the regeneration of nerve fibers into previously-damaged skin. This dual ability of the FK506 derivatives is valuable and unexpected—particularly in view of the fact that numerous other investigators have shown that, in the face of denervation, keratinocyte proliferation falters, and skin breaks down.

In view of the foregoing, the present invention provides a method for promoting healing of a wound in a subject, by administering to the subject an amount of an immunophilin ligand effective to promote healing of the wound in the subject.

The present invention further provides a use of an immunophilin ligand to promote healing of a wound in a subject, wherein the immunophilin ligand is administered to the subject in an amount effective to promote healing of the wound in the subject.

Additionally, the present invention provides a method for promoting regeneration of epithelial tissue in a subject, by administering to the subject an amount of an immunophilin ligand effective to promote regeneration of epithelial tissue in the subject.

Also provided is a use of an immunophilin ligand to promote regeneration of epithelial tissue in a subject, the immunophilin ligand is administered to the subject in an amount effective to promote regeneration of epithelial tissue in the subject.

The present invention is further directed to a method for enhancing epithelial cell proliferation, by contacting epithelial tissue with an amount of an immunophilin ligand effective to enhance epithelial cell proliferation.

The present invention also provides a use of an immunophilin ligand to enhance epithelial cell proliferation, wherein epithelial tissue is contacted with an amount of the immunophilin ligand effective to enhance epithelial cell proliferation.

The present invention is also directed to a method for modulating gene expression in an epithelial cell, by contacting the epithelial cell with an amount of an immunophilin ligand effective to modulate gene expression in the epithelial cell.

Also provided is a use of an immunophilin ligand to modulate gene expression in an epithelial cell, wherein the epithelial cell is contacted with an amount of the immunophilin ligand effective to modulate gene expression in the epithelial cell.

Finally, the present invention provides a method for treating a keratinocyte-associated disorder in a subject in need of treatment therefor, by administering to the subject an amount of an immunophilin ligand effective to treat the keratinocyte-associated disorder in the subject.

Additional aspects of the present invention will be apparent in view of the description that follows.

BRIEF DESCRIPTION OF THE FIGURES

FIG. 5A shows that topical treatment with GM-284 increases the size of adenexal structures, and FIG. 5B illustrates that topical treatment with GM-284 increases the volume of sebaceous cells. (A) Eight days following full-thickness skin biopsies and daily treatment with either vehicle or a 1 µM solution of GM-284, the original biopsy sites were rebiopsied and stained with hemotoxylin and eosin. While the inventor observed no net increase in the number of hair follicles (marked by asterisks) or sebaceous glands (sg), GM-284 treatment increased the size of both structures. A low-power magnification of vehicle-treated skin (panel a) and GM-284-treated skin (panel b) shows the overall increase in hair-follicle size. Higher-power magnification shows an GM-284-mediated increase in the size of sebaceous glands (cf. panels c and d). (B) The plump and full appearance of the sebaceous cells in the GM-284-treated group suggested an overall increase in cell volume. Micrographs from the two treatment groups were scanned, and the volume of sebaceous cells was measured in voxels (n=>300 cells per treatment group). The resulting data were binned by 3000-voxel increments. These data show an overall increase in sebaceous-cell volume, mediated by GM-284. There is an absence of cells smaller than 3000 voxels in the GM-284-treated group, and an absence of cells over 9000 voxels in the vehicle-treated group.

FIG. 7 demonstrates that the effects of GM-284 are reversible. Either GM-284 or vehicle was applied to the dorsal skin on both sides of the animals, daily for 2 weeks. At that time, a 5-mm biopsy was taken from only one side, and all treatment was withheld. After an additional 2-week recovery period, a 5-mm biopsy was taken from the contralateral, intact side. As expected, 2 weeks of treatment with GM-284, over intact, shaved skin, resulted in epidermal hypertrophy, while the vehicle had no effect (top panels). This effect was completely reversed by an additional 2 weeks, when the epidermis had returned to baseline (lower panels). 20×magnification FIG. 8 illustrates that GM-284 alters neuregulin gene expression. Previous work has shown that keratinocytes express neuregulin-α, and that its expression is downregulated following epidermal wounding. As expected, unwounded, vehicle-treated keratinocytes strongly express neuregulin-α (top panel). In contrast, 2 weeks of topical treatment with GM-284 completely downregulated neuregulin-α expression (lower panel). However, allowing the skin to recover for 2 weeks restored keratinocyte expression of neuregulin-α (data not shown). These data are consistent with the notion that GM-284 treatment alters skin biology toward a pro-healing state.

DETAILED DESCRIPTION OF THE INVENTION

Figure 1:
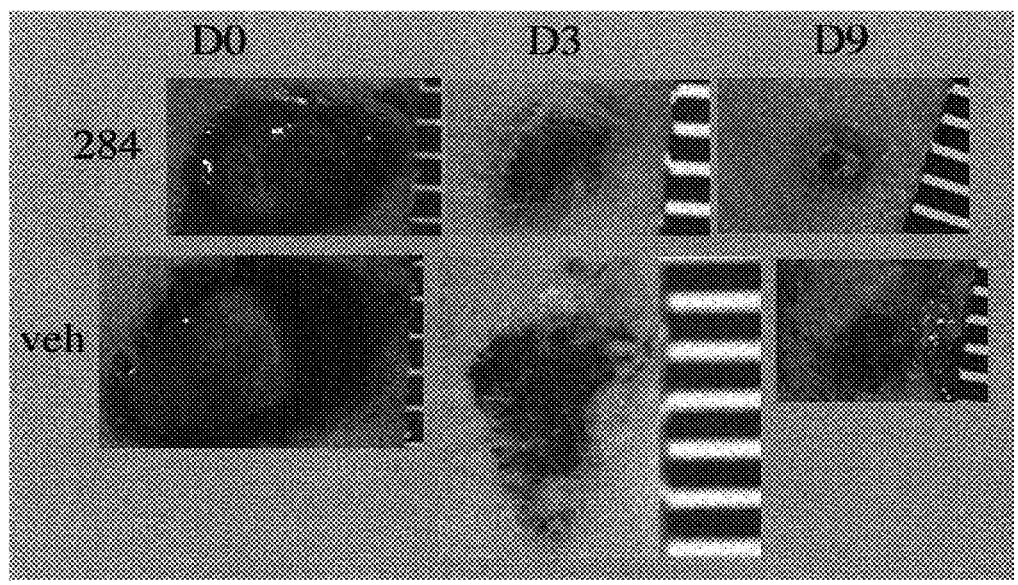
FIG. 1 demonstrates that GM-284 increases the rate at which wounds close. Animals were treated topically with either the vehicle (veh) or GM-284, once daily, for the indicated times. As can be seen, GM-284-treated wounds showed improvement by 3 days (D3), and were virtually closed by the ninth day (D9).

The inventor has recently described studies that elucidated a novel, nonimmunosuppressive immunophilin ligand, termed GM-284—a derivative of the immunosuppressive drug FK506—that enhances axonal regeneration and induces hypermyelination following mechanical transection of peripheral nerves. In particular, the studies demonstrated that GM-284-enhanced nerve regeneration is a Schwann-cell-dependent effect. During these studies, the inventor serendipitously observed that the surgical wounds of animals treated systemically with GM-284 appeared dramatically different from those of either vehicle- or FK506-treated mice. More detailed analysis demonstrated unequivocally that the wounds of mice treated with GM-284 healed at approximately twice the rate as the controls. Given the biochemical properties of GM-284, and the clinical uses of FK506 as a topical medication, the inventor investigated the ability of GM-284 to act as a healing accelerant when applied topically to full-thickness skin biopsies in mice. Results of that investigation revealed that GM-284 has the ability to regenerate wounded epithelial tissue.

Accordingly, the present invention provides a method for promoting healing of a wound in a subject in need of wound healing. As used herein, the term "promoting healing of a wound" means augmenting, improving, increasing, or inducing closure, healing, or repair of a wound. The wound may be the result of any affliction (e.g., disease, injury, surgery), and may be found in any location of the subject (e.g., an internal wound or an external wound). The subject may be any animal, but is preferably a mammal (e.g., humans, domestic animals, and commercial animals). More preferably, the subject is a human.

As disclosed herein, the method of the present invention comprises administering to a subject in need of wound healing an amount of an immunophilin ligand effective to promote healing of the wound in the subject. Immunophilins are ubiquitously-expressed proteins with peptidyl-proline cis/trans isomerase activity (Galat and Metcalfe, Peptidyl-proline cis/trans isomerases. *Prog. Biophys. Mol. Biol.*, 63:67–118, 1995; Marks, A. R., Cellular functions of immunophilins. *Physiol. Rev.*, 76:631–49, 1996). As endogenous intracellular receptors (Kay, J. E., Structure-function relationships in the FK506-binding protein (FKBP) family of peptidylprolyl cis-trans isomerases. *Biochem. J.*, 314:361–85, 1996), immunophilins can be further segregated into two distinct families: FK506-binding proteins (FKBPs) and cyclophilins.

Unless otherwise indicated, an "immunophilin ligand" is an agent that is reactive with an immunophilin. As used herein, "reactive" means the agent has affinity for, binds to, or is directed against an immunophilin. As further used herein, an "agent" shall include a protein, polypeptide, peptide, nucleic acid (including DNA or RNA), antibody, Fab fragment, F(ab')$_2$ fragment, molecule, antibiotic, drug, compound, and any combination thereof. A Fab fragment is a univalent antigen-binding fragment of an antibody, which is produced by papain digestion. A F(ab')$_2$ fragment is a divalent antigen-binding fragment of an antibody, which is produced by pepsin digestion. Additionally, as used herein, the term "immunophilin ligand" refers to immunophilin ligands and any analogues and derivatives thereof, including, for example, a natural or synthetic functional variant of an immunophilin ligand. Preferably, the immunophilin ligand of the present invention is a small molecule that binds an immunophilin receptor.

It is recognized that FK506 binds with high affinity to immunophilins (Kay, J. E., Structure-function relationships in the FK506-binding protein (FKBP) family of peptidyl-prolyl cis-trans isomerases. *Biochem. J.*, 314:361–85, 1996). FK506 (tacrolimus) (Fujisawa Pharmaceutical Co., Ltd, Osaka, Japan) is an immunosuppressive drug that promotes nerve regeneration (Gold, B. G., FK506 and the role of immunophilins in nerve regeneration. *Mol. Neurobiol.*, 15:285–306, 1997; Jost et al., Acceleration of peripheral nerve regeneration following FK506 administration. *Restor. Neurol. Neurosci.*, 17:39–44, 2000). A series of compounds, known as the nonimmunosuppressive immunophilin ligands, have been synthesized on the basis of FK506. Among these compounds are the Vertex drug, V10,367 (Vertex Pharmaceuticals, Cambridge Mass.), the Guilford compound, GPI-1046 (Guilford Pharmaceuticals, Baltimore, Md.), and a novel nonimmunosuppressive ligand disclosed herein, termed GM-284. These FK506 mimetics neither bind to, nor inhibit, calcineurin; therefore, they lack immunosuppressive activity, but retain the proneuroregenerative activities of the parent compound (Steiner et al., Neurotrophic immunophilin ligands stimulate structural and functional recovery in neurodegenerative animal models. *Proc. Natl. Acad. Sci. USA*, 94:2019–24, 1997; Hamilton and Steiner, Immunophilins: beyond immunosuppression. *J. Med. Chem.*, 41:5119–43, 1998).

Figure 9:
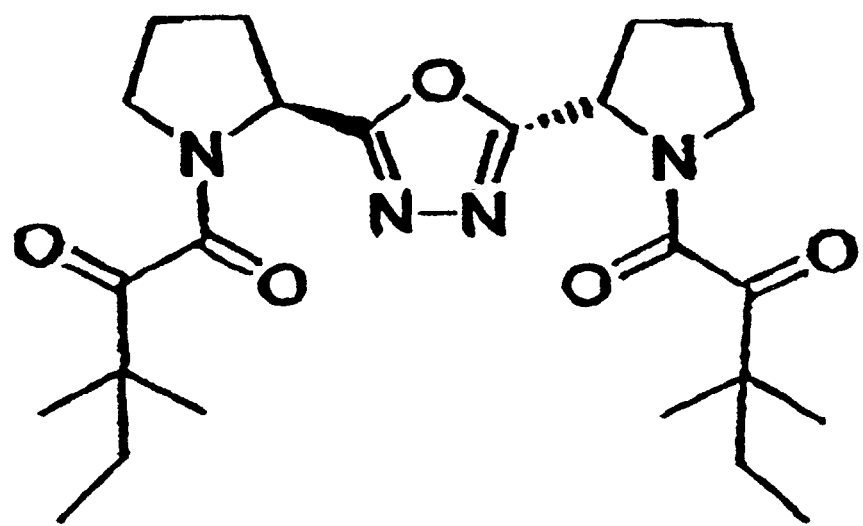
FIG. 9 depicts the structure of GM-284.

Accordingly, in one embodiment of the present invention, the immunophilin ligand is FK506 or an FK506 analogue or derivative. As used herein, an "FK506 derivative" is a chemical substance derived from FK506, either directly or by modification, truncation, or partial substitution. FK506 and its analogues and derivatives may be produced synthetically. The FK506 derivative for use in the present invention may be nonimmunosuppressive. In a preferred embodiment of the present invention, the nonimmunosuppressive FK506 derivative is GM-284. This novel compound is a small molecule that effects transcriptional change in Schwann cells, and promotes wound healing and regeneration of epithelial tissue and nervous tissue, as described below. GM-284 is an immunophilin ligand; its disassociation constant ($k_d$), as a measure of binding affinity for recombinant FKBP52, and as determined by solution-phase tryptophan fluorescence (QTFS), is 139 nm.+−.16.2. The structure of GM-284 is depicted in FIG. 9.

GM-284 may be prepared as follows.

Triethylamine (1.908 g, 2.63 mL, 18.89 mmol) followed by ethyl chloriformate (2.05 g, 1.806 mL, 18.86 mmol) is added to a stirred solution of (2S)-1-(1,2-dioxo-3,3-dimethylpentyl)-2-pyrrolidinecarboxylic acid (4.557 g, 18.89 mmol) in tetrahydrofuran (130 mL) cooled to about −15° C. (MeOH/ice bath). After stirring at about −15° C. to about −10° C. for about 30 min, a solid that is precipitated is removed by filtration and the filtrate and washings are brought to about a volume of 170 mL with the addition of tetrahydrofuran. While stirring the solution of the mixed anhydride (85 mL, 9.32 mmol) at about 0° C., hydrazine monohydrate (0.48 mL, 9.79 mmol) is added. The mixture is stirred and allowed to warm to about RT overnight. After removing the solvent in vacuo, the residue is purified by column chromatography as an eluent to obtain a colorless solid (0.64 g, 28.7% yield) which was recrystallized from ether/pentene mp 177–178° C. CIMS 479 (MH$^+$), 501 (M+Na$^+$) $^1$H NMR (300 MHz, CDCl$_3$, mixture of rotamers) δ (for the major, transrotamer) 9.06 (br s, 2H), 4.61 (m, 2H), 3.50–3.46 (m, 4H), 2.40–2.36 (m, 2H), 2.13–1.94 (m, 6H), 1.83–1.64 (m, 4H), 1.25 and 1.21 (each s, each 6H), 0.87 (t, 3H). IR (KBr)cm$^{-1}$: 3261, 2970, 1706, 1684, 1636. Anal. Calcd. for $C_{24}H_{38}N_4O_6$: C, 60.23; H, 8.00; N, 11.71. Found C, 60.30; N, 11.58.

Pyridine (0.12 mL, 3.35 mmol) followed by thionyl chloride (0.120 mL, 1.66 mmol) is added to a vigorously stirred ice cold slurry of the foregoing colorless solid (0.567 g, 1.185 mmol) in dry ether (400 mL). After stirring the mixture at about 0° C. for about 2 h the precipitated solids are removed by filtration, washed quickly with dry ether and the combined filtrates are evaporated to dryness in vacuo at <40° C. The residue (0.6235 g foam) is dissolved in dry toluene (24 mL) and heated to reflux under nitrogen for about 3 h. The residue obtained by evaporating toluene in vacuo is then purified by column chromatography on silica gel/CH$_2$CL$_2$. Elution with 1% methanol/methylene chloride yields GM 284. GM 284 (0.354 g, 63.6% yield) as a colorless solid, recrystallized from ether/pentene, mp 123–124° C.; $[α]^{24}_D$ −74.6° (c=0.8, CHCL$_3$). CIMS 461 (MH$^+$), 483 (M+Na$^+$). $^1$H NMR (CDCl$_3$, mixture of rotamers) δ (for the major, transrotamer) 5.32 (d,d, J=3.0, 7.6), 3.59 (m 4H), 2.33–2.07 (m 8H), 1.80–1.65 (m, 4H), 1.23 and 1.20 (each s, each 6H), 0.86 (t, 6H). IR (KBr)cm$^{-1}$: 2972, 1704, 1641. Anal. Calcd. for $C_{24}H_{38}N_4O_6$: C, 62.59; H, 7.88; N 12.16, 11.71. Found C, 60.68; H, 7.75; N, 12.14.

GM284 may also be prepared as follows.

Hexamethydisilazane (0.123 mL, 0.585 mM), imidazole (10 mg), and tetrabutyl ammonium fluoride (10 mg) may be added to a solution of the aforesaid colorless solid (0.112 g, 0.234 mM) in chlorobenzene (10 mL), and the mixture heated to reflux under nitrogen for about 72 h. Chromatographic purification of the crude product yields GM-284. [PCT/US00/16221 at page 84]

GM284 may further be prepared as follows.

To a solution of the aforesaid colorless solid (0.2018 g, 0.42 mmol) in tetrahydrofuran (10 mL) may be added (methoxycarbonylsulfamoyl)-triethlyamine hydroxide inner salt (Burgess Reagent total 0.3014 g, 1.265 mmol) in three lots, each added about every 30 min. The mixture is then stirred at about RT for about 72 h. After removing the solvent in vacuo, flash chromatography of the reaction residue yields GM-284 [PCT/US00/16221 at pages 84–85]

GM-284 has been shown to more rapidly restore whisker movement compared to control in rats that have undergone unilateral facial nerve compression with resultant paralyais of the whisker muscle on the affected side.

In the method of the present invention, an immunophilin ligand is administered to a subject in an amount effective to promote healing of a wound in the subject. As used herein, the phrase "effective to promote healing of a wound" means effective to ameliorate or minimize the clinical impairment or symptoms associated with the wound. For example, where the wound is a superficial injury to or cut in the skin of the subject, the clinical impairment or symptoms associated with the wound may be ameliorated or minimized by inducing or accelerating closure of the wound; by promoting regeneration of epithelial tissue at the site of the wound; by enhancing regeneration of at least one damaged neurite at the site of the wound; and/or by enhancing remyelination of at least one damaged neurite at the site of the wound. In one embodiment of the present invention, the effective amount of the immunophilin ligand (e.g., GM-284) is between about 1 mg/kg and about 10 mg/kg. More preferably, the effective amount is about 5 mg/kg. In another embodiment of the present invention, the effective amount of the immunophilin ligand (e.g., GM-284) is between about 0.1 pM and about 5 mM. More preferably, the effective amount is between about 5 pM and about 1.5 mM.

As used herein, the term "promoting regeneration of epithelial tissue" means augmenting, improving, increasing, or inducing partial or full growth or regrowth of epithelial tissue that has degenerated at the site of a wound. As further used herein, the term "growth" refers to an increase in mass, volume, and/or thickness of epithelial tissue, and includes an increase in keratinocyte proliferation. Regeneration, and enhanced regeneration, of epithelial tissue may be measured or detected by known procedures, including assays of blood for markers of wound healing (including collagen subtypes), clinical examination, electron microscopy, gene expression studies, immunohistochemistry, light microscopy, and any of the methods, molecular procedures, and assays disclosed herein. Regeneration of epithelial tissue at the site of a wound may be promoted, for example, by enhancing proliferation of keratinocytes at the site of the wound.

The term "epithelial tissue", as used herein, refers to tissue on the exterior of the body of a subject, or layering its interior surfaces, that is covered by continuous cellular sheets known as epithelial membranes (or epithelia) and the various glands (both exocrine and endocrine) that develop therefrom, and includes, without limitation, any or all of the following: endothelium, mesothelium, and skin (including epidermis and dermis). Examples of cells of the epidermis include, without limitation, Langerhans cells, keratinocytes, and melanocytes. Keratinocytes are committed cells, arising deep in the epidermis, that undergo gradual transformation into scales of keratin as they become displaced toward the surface. Epithelial tissue that produces keratin is referred to herein as "keratinizing epithelial tissue".

As further used herein, the term "enhancing regeneration of a damaged neurite" means augmenting, improving, or increasing partial or full growth or regrowth of a neurite that has degenerated. As further used herein, the term "growth" refers to an increase in diameter, length, mass, and/or thickness of a neurite, a neuron, or myelin, as the case may be. Causes of neurite degeneration include damage to nervous tissue, death of neurons, demyelination, and injury, all associated with a wound in the subject. Regeneration of the neurite may take place in neurites of both the central nervous system and the peripheral nervous system. Regeneration, and enhanced regeneration, of neurites may be measured or detected by known procedures, including Western blotting for myelin-specific and axon-specific proteins, light or electron microscopy in conjunction with morphometry, and any of the methods, molecular procedures, and assays disclosed herein.

Additionally, as used herein, the term "enhancing remyelination of a neurite" means augmenting, improving, or increasing partial or full growth or regrowth of the myelin of a neurite that has degenerated. The remyelination of the neurite may take place in the nerves of both the CNS and the PNS. Remyelination, and enhanced remyelination, of neurites may be measured or detected by known procedures, including Western blotting for myelin-specific and axon-specific proteins, electron microscopy in conjunction with morphometry, and any of the methods, molecular procedures, and assays disclosed herein.

The term "nervous tissue", as used herein, includes the nervous tissue present in both the central nervous system and the peripheral nervous system, and comprises any or all of the following: axons, dendrites, fibrils, fibular processes, ganglion cells, granule cells, grey matter, myelin, neuroglial cells, neurolimma, neuronal cells or neurons, Schwann cells, stellate cells, and white matter. As further used herein, a "neuron" is a conducting or nerve cell of the nervous system that typically consists of a cell body (perikaryon) that contains the nucleus and surrounding cytoplasm; several short, radiating processes (dendrites); and one long process (the axon), which terminates in twig-like branches (telodendrons), and which may have branches (collaterals) projecting along its course. Examples of neurons include, without limitation, autonomic neurons, neurons of the dorsal root ganglia (DRG), enteric neurons, interneurons, motor neurons, peripheral neurons, sensory neurons, and neurons of the spinal cord. In one embodiment of the present invention, the damaged nervous tissue comprises damaged peripheral neurons.

Additionally, as used herein, the term "neurite" refers to processes of neuronal cells, and includes axons and dendrites. For example, the neurite of the present invention may be a process extending from a neuron, such as an autonomic neuron, a neuron of the dorsal root ganglia (DRG), an enteric neuron, an interneuron, a motor neuron, a peripheral neuron, a sensory neuron, or a neuron of the spinal cord. Thus, the neurite may be, for example, an autonomic neuron neurite, a DRG neurite, an enteric neuron neurite, an interneuron neurite, a motor neuron neurite, a peripheral neuron neurite, a sensory neuron neurite, and a neurite of the spinal cord. In one embodiment of the present invention, the neurite is a peripheral neuron neurite.

As demonstrated herein, the immunophilin ligand, GM-284, has the ability to promote wound healing by promoting regeneration of epithelial tissue at the site of the wound; and/or by enhancing regeneration or remyelination of at least one damaged neurite (e.g., a DRG neurite, an interneuron neurite, a motor neuron neurite, a peripheral neuron neurite, a sensory neuron neurite, or a neurite of the spinal cord) at the site of the wound. The amount of immunophilin ligand effective to promote healing of a wound in a subject in need of wound healing will vary depending upon the particular factors of each case, including the type of wound, the severity of the wound, and the method of administration. This amount may be readily determined by the skilled artisan, based upon known procedures, including clinical trials, and methods disclosed herein.

According to the method of the present invention, an immunophilin ligand may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intrathecal, intravascular, intravenous, parenchymatous, or subcutaneous administration), sublingual administration, topical administration, transdermal administration, and administration through an osmotic mini-pump. Preferably, the immunophilin ligand is administered topically.

For oral administration, the formulation of the immunophilin ligand may be presented as capsules, tablets, powders, granules, or as a suspension. The formulation may have conventional additives, such as lactose, mannitol, cornstarch, or potato starch. The formulation also may be presented with binders, such as crystalline cellulose, cellulose derivatives, acacia, cornstarch, or gelatins. Additionally, the formulation may be presented with disintegrators, such as cornstarch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration (i.e., administration by injection through a route other than the alimentary canal), the immunophilin ligand may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampoules or vials. The formulation may be delivered by any mode of injection, including, without limitation, epifascial, intracapsular, intracranial, intracutaneous, intramuscular, intraorbital, intraperitoneal, intraspinal, intrasternal, intrathecal, intravascular, intravenous, parenchymatous, or subcutaneous.

For transdermal administration, the immunophilin ligand may be combined with skin penetration enhancers, such as propylene glycol, polyethylene glycol, isopropanol, ethanol, oleic acid, N-methylpyrrolidone, dimethyl sulfoxide, and the like, which increase the permeability of the skin to the immunophilin ligand, and permit the immunophilin ligand to penetrate through the skin and into the bloodstream. The ligand/enhancer compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The immunophilin ligand may be administered transdermally at the site of the wound in the subject where neural trauma has occurred, or where the wound is localized. Alternatively, the immunophilin ligand may be administered transdermally at a site other than the affected area, in order to achieve systemic administration.

For topical administration, the immunophilin ligand may be combined with additional materials that are known for use in skin-care products, or which are otherwise suitable for topical application. Such optional materials include, but are not limited to, disbursing agents, masking agents, preservatives, processing agents, and additives having specific physicochemical properties, such as polymeric film formers and the like.

The immunophilin ligand of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the immunophilin ligand.

It is within the confines of the present invention that a formulation containing GM-284 may be further associated with a pharmaceutically acceptable carrier, thereby comprising a pharmaceutical composition. Accordingly, the present invention further provides a pharmaceutical composition, comprising GM-284 and a pharmaceutically acceptable carrier. The pharmaceutically acceptable carrier must be "acceptable" in the sense of being compatible with the other ingredients of the composition, and not deleterious to the recipient thereof. Examples of acceptable pharmaceutical carriers include carboxymethylcellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well known in the pharmaceutical arts. For example, GM-284 may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the GM-284 of the present invention to a subject to promote healing of a wound. The GM-284 is provided in an amount that is effective to promote wound healing in a subject to whom the pharmaceutical composition is administered. That amount may be readily determined by the skilled artisan, as described above.

The present invention also provides a method for promoting regeneration of epithelial tissue in a subject. As described above, regeneration of epithelial tissue in a subject may be promoted by enhancing proliferation of keratinocytes in the subject. Accordingly, in one embodiment of the invention, the epithelial tissue is keratinizing epithelial tissue. In a further embodiment of the invention, the regeneration of epithelial tissue is promoted at the site of a wound in the subject, and, thus, contributes to the promotion of wound healing in the subject.

The method of the present invention comprises the step of administering an immunophilin ligand to a subject. In one embodiment of the present invention, the immunophilin ligand is FK506 or an FK506 derivative. The FK506 derivative for use in the present invention may be nonimmunosuppressive. In a preferred embodiment of the present invention, the nonimmunosuppressive FK506 derivative is GM-284. The immunophilin ligand is administered to a subject in an amount effective to promote regeneration of epithelial tissue in the subject, as defined above. In one embodiment of the present invention, the effective amount of the immunophilin ligand (e.g., GM-284) is between about 1 mg/kg and about 10 mg/kg. More preferably, the effective amount is about 5 mg/kg. In another embodiment of the present invention, the effective amount of the immunophilin ligand (e.g., GM-284) is between about 0.1 pM and about 5 mM. More preferably, the effective amount is between about 5 pM and about 1.5 mM.

The present invention further provides a method for enhancing epithelial cell proliferation. As used herein in reference to epithelial cells, the term "enhancing proliferation" means augmenting, improving, or increasing cell division, cell number, and/or growth of epithelial cells, and includes increasing the proliferative rate of keratinocytes and other epithelial cells, as disclosed herein. Enhancement of the growth and proliferation of epithelial cells may be measured or detected by known procedures, including electron microscopy and any of the methods, molecular procedures, and assays disclosed herein. As further used herein, an "epithelial cell" is any cell found in, or derived from, epithelial tissue. Examples of epithelial cells include, without limitation, follicular cells, glandular cells (e.g., sebaceous cells), Langerhans cells, neurons and other neural cells, and skin cells. In a preferred embodiment of the present invention, the epithelial cell is a keratinocyte.

The method of the present invention comprises contacting epithelial tissue with an immunophilin ligand. The epithelial tissue may be damaged or healthy/undamaged. However, in one embodiment of the present invention, the epithelial tissue comprises a wound. In another embodiment of the present invention, the immunophilin ligand is FK506 or an FK506 derivative. The FK506 derivative for use in the present invention may be nonimmunosuppressive. Preferably, the nonimmunosuppressive FK506 derivative is GM-284. The immunophilin ligand is contacted with epithelial tissue in an amount effective to enhance proliferation of at least one epithelial cell. This amount may be determined by the skilled artisan using known procedures (e.g., concentration curves, ELISA, protein-concentration determination, radioimmunoassay, titration curves, and methods disclosed herein.

The method of the present invention may be used to enhance proliferation of at least one epithelial cell in vitro, or in vivo in a subject. For example, an immunophilin ligand may be contacted in vitro with epithelial tissue (e.g., a biopsy or plug of epithelial tissue removed from a subject) by introducing the immunophilin ligand to the tissue using conventional procedures. Alternatively, an immunophilin ligand may be contacted in vivo with epithelial tissue in a subject by administering the immunophilin ligand to the subject. It is also within the confines of the present invention that an immunophilin ligand may be introduced to epithelial tissue in vitro, using conventional procedures, to achieve enhanced proliferation of keratinocytes in vitro. Thereafter, epithelial tissue containing keratinoctyes may be introduced into a subject to provide keratinocytes in vivo. In such an ex vivo approach the epithelial tissue is preferably removed from the subject, subjected to introduction of the immunophilin ligand, and then reintroduced into the subject. In one embodiment of the invention, the enhanced epithelial cell proliferation promotes healing of a wound in the subject.

The ability of immunophilin ligands, particularly FK506 derivatives such as GM-284, to enhance proliferation of keratinocytes in epithelial tissue, as disclosed herein, renders immunophilin ligands particularly useful for treating conditions associated with dysregulation of keratinocyte proliferation. It is believed that immunophilin ligands, including GM-284, would be effective either alone or in combination with other therapeutic agents that are typically used in the treatment of these conditions.

Accordingly, the present invention provides a method for treating a keratinocyte-associated disorder in a subject in need of treatment, comprising contacting epithelial tissue in the subject with an immunophilin ligand (e.g., by administering the immunophilin ligand to the subject), thereby treating the keratinocyte-associated disorder. Keratinocyte-associated disorders that may be treated by methods disclosed herein include disorders characterized by a dysregulation of keratinocyte proliferation (e.g., disorders associated with abnormal keratinocytes, abnormal keratin, or too few keratinocytes).

Examples of keratinocyte-associated disorders include, without limitation, Darier-White's disease; epidermolytic hyperkeratosis; erythema ab igne; IKK gamma/NEMO deficiency; leprosy; a neoplasia (e.g., a carcinoma, such as a basal cell or squamous cell carcinoma; cervical cancer; and oral cancer); periodontal disease; a peripheral neuropathy (including peripheral neuropathies associated with such conditions as acute or chronic inflammatory polyneuropathy, amyotrophic lateral sclerosis (ALS), collagen vascular disorder (e.g., polyarteritis nodosa, rheumatoid arthritis, Sjögren's syndrome, or systemic lupus erythematosus), diphtheria, Guillain-Barré syndrome, hereditary peripheral neuropathy (e.g., Charcot-Marie-Tooth disease (including type I, type II, and all subtypes), hereditary motor and sensory neuropathy (types I, II, and III, and peroneal muscular atrophy), hereditary neuropathy with liability to pressure palsy (HNPP), infectious disease (e.g., acquired immune deficiency syndrome (AIDS)), Lyme disease (e.g., infection with *Borrelia burgdorferi*), invasion of a microorganism (e.g., leprosy), leukodystrophy, metabolic disease or disorder (e.g., amyloidosis, diabetes mellitus, hypothyroidism, porphyria, sarcoidosis, or uremia), neurofibromatosis, nutritional deficiencies, peroneal nerve palsy, polio, porphyria, postpolio syndrome Proteus syndrome, pressure paralysis (e.g., carpal tunnel syndrome), progressive bulbar palsy, radial nerve palsy, spinal muscular atrophy, a toxic agent (e.g., barbital, carbon monoxide, chlorobutanol, dapsone, emetine, heavy metals, hexobarbital, lead, nitrofurantoin, orthodinitrophenal, phenytoin, pyridoxine, sulfonamides, triorthocresyl phosphate, the vinca alkaloids, many solvents, other industrial poisons, and certain AIDS drugs (including didanosine and zalcitabine), trauma (including neural trauma—the leading cause of peripheral neuropathy, worldwide), and ulnar nerve palsy (Beers and Berkow, eds., *The Merck Manual of Diagnosis and Therapy*, $17^{th}$ ed. (Whitehouse Station, N.J.: Merck Research Laboratories, 1999) chap. 183); porokeratosis; a pressure ulcer; psoriasis; striate palmoplantar keratoderma; a skin ulceration (e.g., a diabetic ulcer); a venous stasis ulcer; and a wound. In a preferred embodiment, the keratinocyte-associated disorder is leprosy, periodontal disease, a peripheral neuropathy, a pressure ulcer, psoriasis, a skin ulceration, a venous stasis ulcer, or a wound.

In the method of the present invention, an immunophilin ligand is contacted with epithelial tissue in a subject (e.g., administered to a subject), for the purpose of treating a keratinocyte-associated disorder, in an amount effective to enhance proliferation of at least one epithelial cell. In one embodiment of the present invention, the effective amount of the immunophilin ligand (e.g., GM-284) is between about 0.1 pM and about 5 mM. More preferably, the effective amount is between about 5 pM and about 1.5 mM.

Previous work has shown that keratinocytes express neuregulin-α, and that its expression is downregulated following epidermal wounding. In the present study, the inventor has demonstrated that neuregulin-α is downregulated by the immunophilin ligand, GM-284. These findings are consistent with the notion that GM-284 treatment alters skin biology toward a pro-healing state. In view of the foregoing, the present invention further provides a method for modulating gene expression in an epithelial cell, by contacting the epithelial cell with an immunophilin ligand.

As used herein, the term "modulating gene expression" includes altering gene expression by increasing or upregulating gene expression, or by decreasing or downregulating gene expression. By way of example, the expression of an epithelial cell gene may be modulated by contacting an epithelial cell with an immunophilin ligand. Examples of epithelial cell genes that may be modulated by the method of the present invention include, without limitation, a neuregulin and interleukin-1 homologue 1. In one embodiment of the present invention, the neuregulin is neuregulin-α. In a further embodiment of the invention, the neuregulin is neuregulin-α and its expression is downregulated. Modulation of gene expression in epithelial cells may be measured or detected by known procedures, including cDNA-array assays of gene expression, Northern blotting, and any of the methods, molecular procedures, and assays disclosed herein.

Examples of epithelial cells in which gene expression may be modulated include, without limitation, follicular cells, glandular cells (e.g., sebaceous cells), Langerhans cells, neurons and other neural cells, and skin cells. In a preferred embodiment of the present invention, the epithelial cell is a keratinocyte. The epithelial cell may be, for example, in epithelial tissue. In the method of the present invention, the epithelial cell is contacted with an amount of immunophilin ligand effective to modulate gene expression in the epithelial cell. This amount may be readily determined by the skilled artisan, based upon known procedures, including analysis of in vivo dose curves and electron microscopy, and methods disclosed herein.

The method of the present invention may be used to modulate gene expression in an epithelial cell in vitro, ex vivo, or in vivo in a subject, in accordance with methods described above. In one embodiment of the present invention, the immunophilin ligand is FK506 or an FK506 derivative. The FK506 derivative for use in the present invention may be nonimmunosuppressive. In a preferred embodiment of the present invention, the nonimmunosuppressive FK506 derivative is GM-284.

It is believed that, by modulating gene expression in epithelial cells, immunophilin ligands will be useful for the treatment of conditions associated with dysregulation of keratinocyte proliferation. It is further believed that immunophilin ligands, including GM-284, would be effective either alone or in combination with other therapeutic agents that are typically used in the treatment of these conditions.

Accordingly, the present invention provides a method for treating a keratinocyte-associated disorder in a subject in need of treatment, comprising contacting an epithelial cell in the subject with an immunophilin ligand (e.g., by administering the immunophilin ligand to the subject), thereby treating the keratinocyte-associated disorder. Examples of keratinocyte-associated disorders that may be treated by the method of the present invention are discussed above. In a preferred embodiment of the present invention, the keratinocyte-associated disorder is leprosy, periodontal disease, a peripheral neuropathy, a pressure ulcer, psoriasis, a skin ulceration, a venous stasis ulcer, or a wound.

In the method of the present invention, an immunophilin ligand is contacted with an epithelial cell in a subject (e.g., administered to a subject), for the purpose of treating a keratinocyte-associated disorder, in an amount effective to modulate gene expression in the epithelial cell. In one embodiment of the present invention, the effective amount of the immunophilin ligand (e.g., GM-284) is between about 0.1 pM and about 5 mM. More preferably, the effective amount is between about 5 pM and about 1.5 mM.

The present invention also provides a method for treating a keratinocyte-associated disorder in a subject in need of treatment, by administering an immunophilin ligand to the subject, as described above. Examples of keratinocyte-associated disorders that may be treated by the method of the present invention are discussed above. In a preferred embodiment of the present invention, the keratinocyte-associated disorder is leprosy, periodontal disease, a peripheral neuropathy, a pressure ulcer, psoriasis, a skin ulceration, a venous stasis ulcer, or a wound. In one embodiment of the present invention, the immunophilin ligand is FK506 or an FK506 derivative. The FK506 derivative for use in the present invention may be nonimmunosuppressive. In a preferred embodiment of the invention, the nonimmunosuppressive FK506 derivative is GM-284.

The immunophilin ligand of the present invention is administered to a subject in need of treatment for a keratinocyte-associated disorder in an amount that is effective to treat the keratinocyte-associated disorder in the subject. As used herein, the phrase "effective to treat a keratinocyte-associated disorder" means effective to ameliorate or minimize the clinical impairment or symptoms of the keratinocyte-associated disorder. For example, where the keratinocyte-associated disorder is a peripheral neuropathy, the clinical impairment or symptoms of the peripheral neuropathy may be ameliorated or minimized by alleviating vasomotor symptoms, increasing deep tendon reflexes, reducing muscle atrophy, restoring sensory function, and strengthening muscles. The amount of immunophilin ligand effective to treat a keratinocyte-associated disorder in a subject in need of treatment therefor will vary depending upon the particular factors of each case, including the type of keratinocyte-associated disorder, the stage of the keratinocyte-associated disorder, the subject's weight, the severity of the subject's condition, and the method of administration. This amount may be readily determined by the skilled artisan, based upon known procedures, including clinical trials, and methods disclosed herein.

The present invention is described in the following Examples, which are set forth to aid in the understanding of the invention, and should not be construed to limit in any way the scope of the invention as defined in the claims which follow thereafter.

EXAMPLES

Example 1

GM-284 Promotes Wound Healing

In recent studies, the inventor demonstrated myelin and axonal hypertrophy following mechanical transection of the sciatic nerve. These studies required surgical exposure of the right lower quadrant of all study animals. Following exposure of the sciatic nerve from the sciatic notch to the knee, and manipulation of the nerve, the muscle and overlaying skin were closed with suture material. Each animal was subsequently treated with a daily gavage of either GM-284 (5 mg/kg), FK506 (5 mg/kg), or methylcellulose vehicle alone. During the post-operative course, it was noted by an investigator who was blinded to the treatment groups that the surgical wounds of one group of animals appeared to be qualitatively improved over those of the other two groups, with less erythemia and more rapid closure. Following unblinding of the investigator, it was learned that the group demonstrating improved healing had received treatment with GM-284.

To determine whether GM-284 had a direct effect on the skin, or whether the enhanced wound closure was an indirect effect of GM-284 that was influenced by healing of the underlying muscle, the experiments were repeated, with one exception: only the skin was entered, and the muscle and overlying fascia were left intact. Under these conditions, the skin of GM-284-treated animals showed the same improved healing characteristics as were demonstrated when the muscle was also involved, suggesting that GM-284 acts directly on the skin proper.

The foregoing results also raised the possibility that GM-284 might show similar effects if administered topically, directly to the surgical site. To investigate this possibility, 10 retired breeders—5 male mice and 5 female mice—were prepared for surgery, and were subjected to 5-mm skin biopsies using a disposable biopsy punch. After achieving hemostasis, the wounds were treated immediately with topical application of either GM-284 or vehicle, or received no treatment at all. The treatment was repeated daily. As shown in FIG. 1, the GM-284-treated wounds, by 3 days, were significantly more closed than the control groups. By 9 days, the GM-284-treated wounds were virtually closed. Furthermore, the edges of the GM-284-treated wounds appeared to be better granulated than the controls (cf. the GM-284-treated skin and the control skin on D3 and D9 in FIG. 1).

Figure 2:
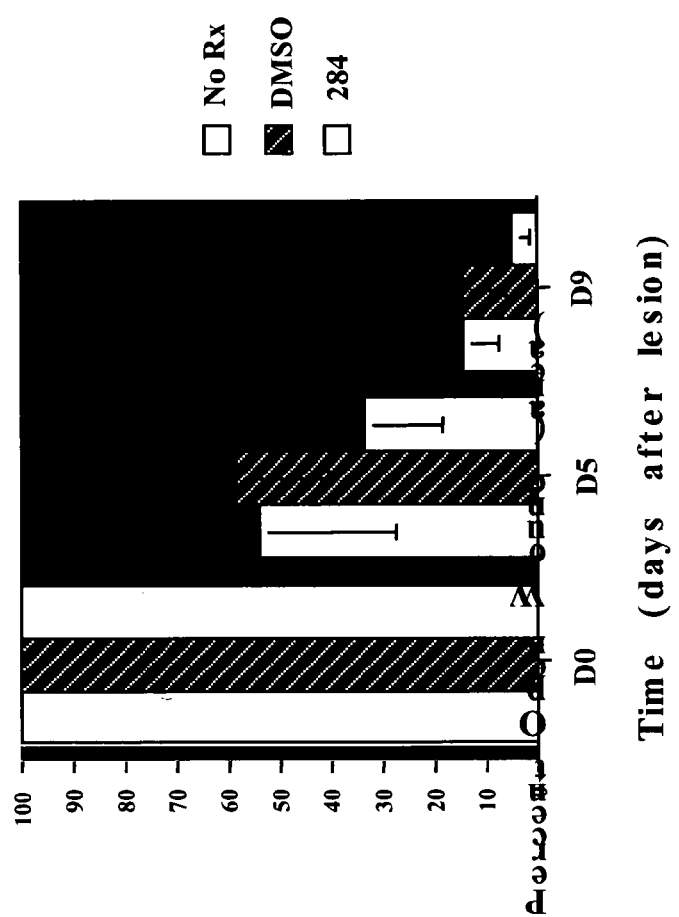
FIG. 2 depicts quantification of GM-284-mediated skin closure. The wounds of every animal in the treatment groups were photographed at the indicated times, and the area of each open wound was measured using the image-analysis program, NIH Image. As can be seen, there was a large difference in the closure rates by day 5. By day 9, the GM284-treated skin was approximately as completely healed as that of the two control groups.

During the experimental period, the wounds were photographed daily, and the photographs were scanned for volume analysis. The open area of each wound was quantified using an image-analysis program, NIH Image. By the third treatment day, the GM-284-treated wounds had closed approximately twice as fast as the control groups. The increased rate of GM-284-mediated wound closure was maintained at 9 days, when the wounds were approximately one-third the size of those of the control groups (FIG. 2).

Example 2

GM-284 Doubles the Keratinocyte Proliferative Index

Figure 3:
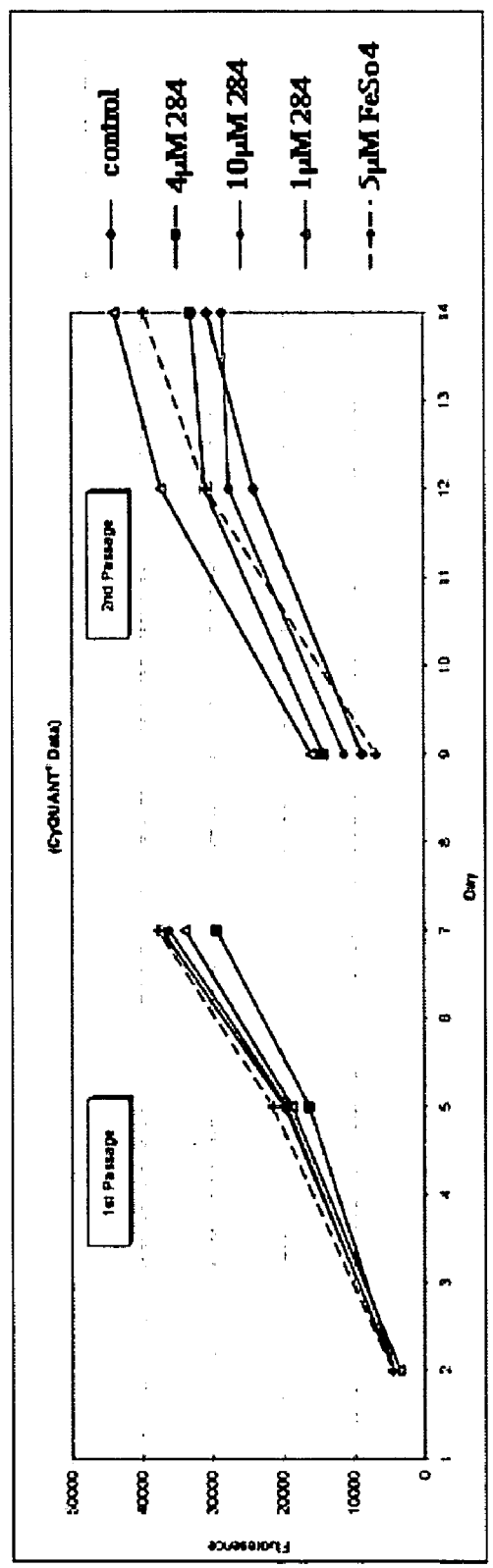
FIG. 3 shows that GM-284 doubles the proliferative rate of human keratinocytes. Human keratinocytes were thawed, then either grown in the presence of increasing concentrations of GM-284, or grown in 5 µM $FeSO_4$ as a positive control. No difference was seen in proliferation before the first passage of cells, which is usual. However, after the cells were reseeded and then grown in the indicated concentrations of GM-284, a doubling of the proliferative index of cells grown in the presence of 1 µM GM-284 was observed.

As detailed above, keratinocyte proliferation is influenced by a number of factors, including innervation (Hsieh and Lin, Modulation of keratinocyte proliferation by skin innervation. *J. Invest. Dermatol.*, 113:579–86, 1999) and growth-factor treatment (Castagnino et al., Neu differentiation factor/heregulin induction by hepatocyte and keratinocyte growth factors. *Oncogene*, 19:640–48, 2000; and reviewed by Werner and Smola, Paracrine regulation of keratinocyte proliferation and differentiation. *Trends Cell Biol.*, 11: 143–46, 2001). Thus, by culturing human-foreskin keratinocytes with increasing concentrations of GM-284, the inventor investigated the possibility that GM-284 was able to influence keratinocyte growth. As shown in FIG. 3, treatment with 1 µM of GM-284 increased the rate of keratinocyte proliferation by more than 150% after 14 days of treatment. Not surprisingly, a comparison of the growth rates of keratinocytes grown in 1 µM or 10 µM GM-284 showed that the increased drug concentration completely ablated the pro-proliferative activity observed at 1 µM. This type of drug-dependent inhibition is consistent with the inventor's previous observation that a higher concentration of GM-284 blocks gene expression that is induced at a lower drug concentration (data not shown). Importantly, these data demonstrate that GM-284 has a direct effect on keratinocytes, and also has an effect on the underlying nerves (see below).

Example 3

Topical Treatment with GM-284 Increases Epidermal Thickness In Vivo

Figure 4:
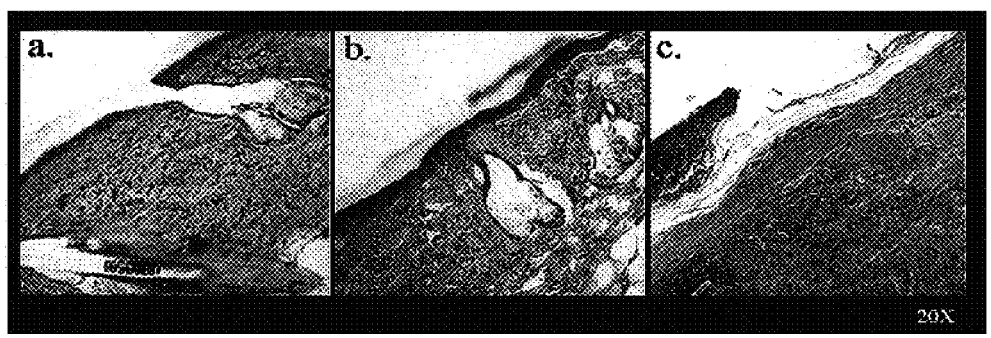
FIG. 4 illustrates that topical treatment with GM-284 increases epidermal thickness in vivo. Eight days after full-thickness skin biopsies and daily treatment with vehicle, FK506, or GM-284, the original biopsy sites were rebiopsied and stained with hemotoxylin and eosin. There was no apparent difference in the epidermal thickness of the vehicle-treated skin (panel a) or FK506-treated skin (panel b). In contrast, the GM-284-treated skin showed a marked increase in epidermal thickness (panel c).

The increased rate of wound closure in the presence of GM-284, taken with the accelerated keratinocyte proliferation, suggested to the inventor the possibility that GM-284 treatment might alter epidermal thickness in vivo. To examine this possibility, 5-mm, full-skin thickness biopsies were taken from the hindquarters of both male and female ICR retired breeders. The wounds were treated daily, for 8 days, with topical administration of either the DMSO-based vehicle, or FK506 or GM-284 in the vehicle. Thereafter, the original biopsy site was rebiopsied. Comparison of epidermal thickness of the FK506- and vehicle-treated animals showed no observable differences (cf. FIG. 4, panels a and b). In contrast, the epidermis of the GM-284-treated animals was much thicker, and appeared to be much more cellular, than the epidermis of animals under the other two conditions (FIG. 4, panel c). Without being bound by theory, it is believed that, given the GM-284-mediated increase in keratinocyte proliferation, the in vivo epidermal hypertrophy demonstrated herein was a result of GM-284-induced increases in keratinocyte proliferation.

Example 4

Topical Treatment of Wounds with GM-284 Induces Hypertrophy of Adenexal Structures In addition to the increased epidermal thickness demonstrated above, treatment with GM-284 also affects intradermal structures. Using the topical-application-following-skin-biopsy paradigm detailed above, the lateral aspects of the original lesions were rebiopsied 8 days after the original lesions. The tissues were immersion-fixed, dehydrated through step gradients of alcohols, stained with hemotoxylin and eosin, and mounted for microscopic analysis, all following standard protocols. It is known that skin wounds in rodents heal inwards, from the perimeter, converging at a central point (Cohen, Stress and wound healing. *Acta Anat.* (*Basel*), 103:134–41, 1979). Therefore, the lateral edges of the original lesions were selected for analysis because these areas of tissue had the greatest opportunity to regenerate under the experimental conditions.

While there was no apparent difference in the regularity of the adenexal structures in the GM-284-treated skin, as compared with that of the vehicle control, there was a large increase in the width and cellularity of the basal aspects of the hair follicles (FIG. 5A, panels a and b). In addition, the sebaceous glands of the GM-284-treated skin appeared to be much rounder, larger, and fuller than those of the controls. Higher-power magnification of these structures shows both an increase in sebaceous gland cell number and an apparent increase in the cytoplasmic content of the cells (FIG. 5A, panels c and d).

The volumes of the cells of the sebaceous glands were determined by scanning micrographs taken from animals treated with either GM-284 or vehicle for 8 days, and measuring cell size with the NIH Image program. As shown in FIG. 5B, when the cell volumes were binned according to size, there was a marked shift to the right as a result of GM-284 treatment. There was an absence of smaller sebaceous cells in the GM-284 treatment group, and an absence of larger cells in the vehicle-treated group. The increases in the cellularity of the adenexal structures of the GM-284-treated skin was not surprising, as recent reports have demonstrated a common stem cell which gives rise to keratinocytes, follicular cells, and sebaceous cells, and which resides in the "bulge" at the lateral aspect of the hair follicle (Taylor et al., Involvement of follicular stem cells in forming not only the follicle but also the epidermis. *Cell*, 102:451–61, 2000; Merrill et al., Tcf3 and Lef1 regulate lineage differentiation of multipotent stem cells in skin. *Genes Dev.*, 15:1688–05, 2001). Thus, given the cellular expansion in all three of these dermal compartments, it is likely that GM-284 acts at the level of the common stem cell.

Example 5

GM-284 Induces Rapid Reinnervation and Remyelination of Healing Skin

In the absence of normalizing dermal histoarchitecture, the permanent reepithelialization of skin ulcers is difficult. There is a huge body of literature on this topic: a search by the inventor of the words "skin" and "ulcer", in papers published between 1963 and the present, yielded 8545 articles on the subject, many of which address the issues that are raised herein. Clearly, the involvement of the nervous system in chronic skin ulcers has been understood for at least 40 years; yet, the successful treatment of these wounds, to date, has been elusive.

As shown above, GM-284 induces rapid healing of wounds; it does so, in part, by influencing the proliferation of cells within the dermis and epidermis. In addition, this compound has profound effects on the regeneration of peripheral nerves. The inventor has previously shown that, following crushing-nerve injury, GM-284 enhances nerve regeneration, acting on both the axon and the Schwann cell (data not shown). To investigate whether GM-284 also enhances sensory-nerve regeneration into skin following wounding, the inventor examined innervation of skin biopsies after 8 days of treatment with either GM-284 or vehicle.

Skin sections were stained with an antibody that recognizes either myelin basic protein (MBP) or a neuron-specific isoform of β-tubulin (Easter et al., Initial tract formation in the mouse brain. *J. of Neurosci.*, 13:285–99, 1993). Staining of normal skin from the dorsal trunk of the mouse showed small, MBP-positive myelinated fibers which course parallel to the epidermis. As described previously, Langerhans cells—antigen-presenting cells residing in the skin (Steinman and Inaba, The binding of antigen presenting cells to T lymphocytes. *Adv. Exp. Med. Biol.*, 237:31–41, 1988)—are aligned in parallel along the nerve fibers of the skin (Asahina et al., Modulation of Langerhans cell function by epidermal nerves. *J. Allergy Clin. Immunol.*, 96:1178–82, 1995) (FIG. 6A, left panel). After 8 days of treatment with GM-284 following injury, skin regained its pre-injury histology, with new, myelinated fibers running parallel to the epidermis and the Langerhans cells (FIG. 6A, middle panel). In contrast, healing skin, which had been treated with vehicle alone, still had no myelinated fibers, nor did the Langerhans cells appear to have any apparent organization relative to the epidermis (FIG. 6A, right panel).

Figure 6B:
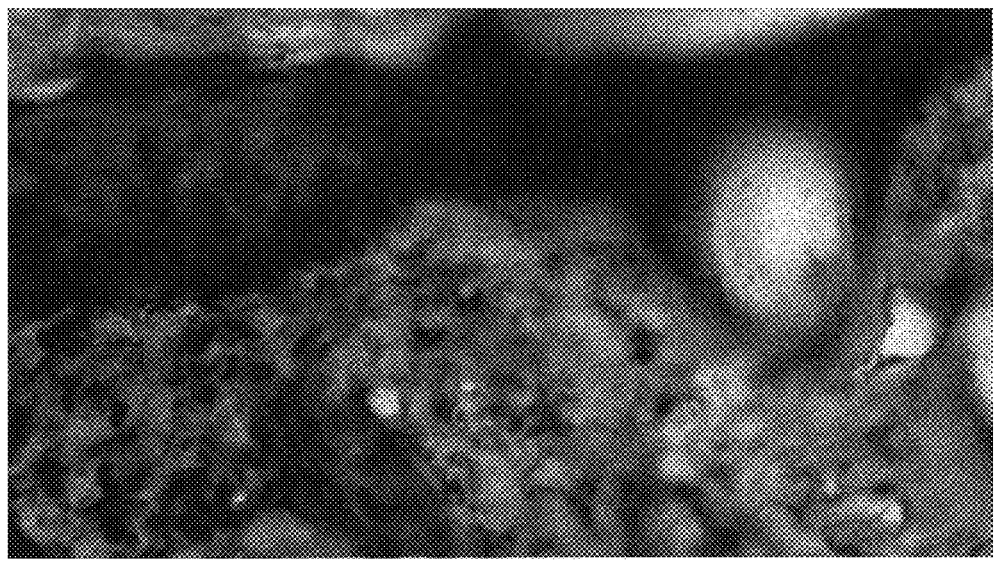
FIG. 6 illustrates that GM-284 induces rapid reinnervation of injured skin. (A) The inventor examined innervation of surgically damaged skin (biopsy) following 8 days of treatment with either GM-284 or vehicle. The skin sections were stained with an antibody that recognizes myelin basic protein (MBP). Staining of normal, naive skin from the dorsal trunk of the mouse showed small, MBP-positive myelinated fibers that coursed parallel to the epidermis, and, along with Langerhans cells (LC), aligned in parallel along the nerve fibers of the skin (left panel). After 8 days of treatment with GM-284 following injury, the skin regained its pre-injury histology, with new, myelinated fibers running parallel to the epidermis and the Langerhans cells (middle panel). In contrast, healing skin which had been treated with vehicle alone still had no myelinated fibers, nor did the Langerhans cells appear to have any organization relative to the epidermis (right panel). (B) Unmyelinated fibers also innervate the skin, where the fibers extend into the epidermis. Consistent with findings of GM-284-promoted regeneration of the myelinated fibers, it was discovered that the compound also promotes regeneration of naked axons into the epidermis. No such fibers were found in the vehicle-treated controls.

In addition to the myelinated fibers shown above, there are also unmyelinated fibers that innervate the skin. These fibers extend into the epidermis, where they contribute to nociception and skin cooling (Light and Perl, "Peripheral Sensory Systems". In *Peripheral Neuropathy*, Dyck, P. J. and Thomas, P. K., eds. (Philadelphia: W.B. Saunders Company, 1993). Consistent with findings of GM-284-promoted regeneration of myelinated fibers, it was discovered herein that the compound also promotes regeneration of naked axons into the epidermis (FIG. 6B). No such fibers were found in the vehicle-treated controls.

Taken together, the foregoing data show that GM-284 promotes dermal nerve regeneration, and also acts independently on keratinocytes. However, it is likely that the GM-284-promoted reinnervation shown herein also contributes to the epidermal thickening shown in FIG. 4.

Example 6

Treatment of Intact Skin with GM-284 Induces a Reversible Epidermal Hypertrophy

The changes in regenerating skin demonstrated above raise questions concerning the effects of GM-284 on intact dermal structures. In order to test these effects, the inventor shaved the dorsal fur from over the hindquarters, bilaterally, and tattooed ~5-mm circles on the skin. Either GM-284 or vehicle was applied daily, to both sides of the animals, for 2 weeks. After that time, a 5-mm biopsy was taken from only one side of each animal, and all treatment was withheld. After an additional 2-week "recovery period", a 5-mm biopsy was taken from the intact side of each animal. Two weeks of treatment with GM-284, over intact skin, resulted in epidermal hypertrophy, as shown in FIG. 7 (top panels). This effect was completely reversed by the end of 2 more weeks, when the epidermis had returned to baseline (FIG. 7, lower panels).

Example 7

GM-284 Alters Gene Expression of Neuregulin In situ and Induces a Healing-like State in Keratinocytes in the Absence of Injury The neuregulins are a large family of EGF-related growth factors that, along with their receptors, the erbB tyrosine kinases, have been implicated in a large number of biologies (Xian and Zhou, Roles of transforming growth factor-alpha and related molecules in the nervous system. *Mol. Neurobiol.*, 20:157–83, 1999; Adlkofer and Lai, Role of neuregulins in glial cell development. *Glia*, 29:104–11, 2000; Niemann et al., Hepatocyte growth factor and neuregulin in mammary gland cell morphogenesis. *Adv. Exp. Med. Biol.*, 480:9–18, 2000), including mediation of axon/Schwann cell interactions. The inventor has previously shown that neuregulins influence Schwann cell gene expression, during both development and regeneration (Wu et al., The POU gene brn-5 is induced by neuregulin and is restricted to myelinating Schwann cells. *Mol. Cell Neurosci.*, 17:683–95, 2001). The inventor has also shown that GM-284 affects Schwann cell gene expression, and enhances Schwann-cell-mediated nerve regeneration.

As demonstrated above, GM-284 induces rapid re-entry of nerve fibers into skin and accelerates wound healing. Previous work has shown that keratinocytes express neuregulin-α, and that its expression is downregulated following epidermal wounding (Danilenko et al., Neu differentiation factor upregulates epidermal migration and integrin expression in excisional wounds. *J. Clin. Invest.*, 95:842–51, 1995). As expected, unwounded, vehicle-treated keratinocytes strongly expressed neuregulin-α (FIG. 8, top panel). In contrast, 2 weeks of topical treatment with GM-284 completely downregulated neuregulin-α expression (FIG. 8, lower panel). However, when the skin was allowed to recover for 2 weeks, keratinocyte expression of neuregulin-α was restored (data not shown). These data are consistent with the notion that GM-284 treatment alters skin biology toward a pro-healing state.

Homeostasis of skin depends upon a complex biology that involves an active interplay between keratinocytes and the peripheral nerves that infiltrate and supply target areas. Loss of innervation, either following trauma or due to pathology, results in a decrease in keratinocyte proliferation and a thinning of the epidermis (Lauria et al., Neuropathological alterations in diabetic truncal neuropathy: evaluation by skin biopsy. *J. Neurol. Neurosurg. Psychiatry*, 65:762–66, 1998; Hsieh and Lin, Modulation of keratinocyte proliferation by skin innervation. *J. Invest. Dermatol.*, 113:579–86, 1999). Importantly, these effects are reversible, with epidermal thickness normalizing concomitantly with reinnervation (Huang et al., Influence of cutaneous nerves on keratinocyte proliferation and epidermal thickness in mice. *Neuroscience*, 94:965–73, 1999).

In the above Examples, the inventor has demonstrated that a novel, nonimmunosuppressive immunophilin ligand, GM-284, affects both components of the regenerating skin: the keratinocytes and the peripheral nerves. These effects cooperate to increase the rate at which wounds heal, by increasing keratinocyte proliferation directly and increasing dermal nerve regeneration directly. In particular, the inventor's data show that treatment with GM-284 corrects the underlying defects in wounded skin by acting on the skin adenexa, as well as on keratinocytes and nerves. These findings are of great interest as efforts increase to generate artificial, or "lab grown", skin grafts from autologous donors. Data from Taylor et al. (Involvement of follicular stem cells in forming not only the follicle but also the epidermis. *Cell*, 102:451–61, 2000) and Merrill et al. (Tcf3 and Lef1 regulate lineage differentiation of multipotent stem cells in skin. *Genes Dev.*, 15:1688–05, 2001) suggest that all three dermal components—keratinocytes, sebaceous cells, and hair follicles—share a common stem cell. Therefore, an agent such as GM-284 might prove an important adjunct in the generation of artificial skin containing the appropriate structures.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for promoting healing of a wound in a subject, comprising the step of administering to the subject an amount of 2,2'-(1,3,4-oxadiazole-2,5-diyl)bis[1-(3,3-dimethyl-1,2-dioxopentyl)-pyrrolidine, GM-284, effective to promote healing of the wound in the subject.

2. The method of claim 1, wherein wound healing is promoted in the subject by promoting regeneration of epithelial tissue at the site of the wound.

3. The method of claim 2, wherein regeneration of epithelial tissue at the site of the wound in the subject is promoted by enhancing proliferation of keratinocytes at the site of the wound.

4. The method of claim 1, wherein wound healing is promoted in the subject by enhancing regeneration of at least one damaged neurite at the site of the wound.

5. The method of claim 4, wherein the neurite is selected from the group consisting of an autonomic neuron neurite, a DRG neurite, an enteric neuron neurite, an interneuron neurite, a motor neuron neurite, a peripheral neuron neurite, a sensory neuron neurite, and a neurite of the spinal cord.

6. The method of claim 1, wherein wound healing is promoted in the subject by enhancing remyelination of at least one damaged neurite at the site of the wound in the subject.

7. The method of claim 6, wherein the neurite is selected from the group consisting of an autonomic neuron neurite, a DRG neurite, an enteric neuron neurite, an interneuron neurite, a motor neuron neurite, a peripheral neuron neurite, a sensory neuron neurite, and a neurite of the spinal cord.

8. The method of claim 1, wherein the subject is a mammal.

9. The method of claim 8, wherein the mammal is a human.

10. The method of claim 1, wherein the amount of GM-284 is between about 1 mg/kg and about 10 mg/kg.

11. The method of claim 10, wherein the amount of GM-284 is about 5 mg/kg.

12. The method of claim 1, wherein the amount of GM-284 is between about 0.1pM and about 5 mM.

13. The method of claim 12, wherein the amount of GM-284 is between about 5 pM and about 1.5 mM.

14. The method of claim 1, wherein the GM-284 is administered to the subject by oral administration, parenteral administration, sublingual administration, topical administration, transdermal administration, or osmotic pump.

15. The method of claim 14, wherein the GM-284 is administered to the subject by topical administration.

16. A method for promoting regeneration of epithelial tissue in a subject, comprising the step of administering to the subject an amount of 2,2'-(1,3,4-oxadiazole-2,5-diyl)bis[1-(3,3-dimethyl-1,2-dioxopentyl)-pyrrolidine, GM-284, effective to promote regeneration of epithelial tissue in the subject.

17. The method of claim 16, wherein the epithelial tissue is keratinizing epithelial tissue.

18. The method of claim 16, wherein regeneration of epithelial tissue in the subject is promoted by enhancing proliferation of keratinocytes in the subject.

19. The method of claim 16, wherein regeneration of epithelial tissue is promoted at the site of a wound in the subject.

20. The method of claim 16, wherein the subject is a mammal.

21. The method of claim 20, wherein the mammal is a human.

22. The method of claim 16, wherein the amount of GM-284 is between about 1 mg/kg and about 10 mg/kg.

23. The method of claim 22, wherein the amount of GM-284 is about 5 mg/kg.

24. The method of claim 16, wherein the amount of GM-284 is between about 0.1 pM and about 5 mM.

25. The method of claim 24, wherein the amount of GM-284 is between about 5 pM and about 1.5 mM.

26. The method of claim 16, wherein the GM-284 is administered to the subject by oral administration, parenteral administration, sublingual administration, topical administration, transdermal administration, or osmotic pump.

27. The method of claim 26, wherein the GM-284 is administered to the subject by topical administration.

* * * * *